US006626819B2

(12) United States Patent
Wallace

(10) Patent No.: US 6,626,819 B2
(45) Date of Patent: Sep. 30, 2003

(54) PERMANENT MAGNETIC AND ELECTROMAGNETIC APPARATUS FOR EMBOLIZING AN ANEURYSM WITH MAGNETICALLY CONTROLLABLE EMBOLIC AND METHOD

(75) Inventor: Ian Wallace, Madison, WI (US)

(73) Assignee: SciMed Life Systems, Inc., Maple Grove, MN (US)

(*) Notice: Subject to any disclaimer, the term of this patent is extended or adjusted under 35 U.S.C. 154(b) by 160 days.

(21) Appl. No.: 09/759,617

(22) Filed: Jan. 12, 2001

(65) Prior Publication Data
US 2003/0114727 A1 Jun. 19, 2003

(51) Int. Cl.$^7$ .......................... A61M 37/00; A61N 2/00
(52) U.S. Cl. ....................................................... 600/12
(58) Field of Search ................... 600/12, 9, 11, 600/585, 433, 13–15; 128/899; 606/130, 32, 108, 198; 601/9; 424/9; 604/276, 95, 264, 253, 19, 48

(56) References Cited

U.S. PATENT DOCUMENTS

| 5,122,136 A | 6/1992 | Guglielmi et al. |
| 5,250,071 A | 10/1993 | Palermo |
| 6,014,580 A | 1/2000 | Blume et al. |
| 6,123,714 A | 9/2000 | Gia et al. |
| 6,315,709 B1 * | 11/2001 | Garibaldi et al. .............. 600/12 |
| 6,364,823 B1 * | 4/2002 | Garibaldi et al. .............. 600/12 |
| 6,375,606 B1 * | 4/2002 | Garibaldi et al. .............. 600/12 |
| 6,401,723 B1 * | 6/2002 | Garibaldi et al. ........... 128/899 |

FOREIGN PATENT DOCUMENTS

| WO | WO 00 54835 A | 9/2000 |
| WO | WO 01 15608 A | 3/2001 |

OTHER PUBLICATIONS

Roth, David A. "Occlusion of Intracranial Aneurysms by Ferromagnetic Thrombi" Journal of Applied Physics, vol. 40, No. 3, Mar. 1, 1969, pp. 1044–1045.

* cited by examiner

Primary Examiner—Max F. Hindenburg
Assistant Examiner—Brian Szmal
(74) Attorney, Agent, or Firm—Bingham McCutchen LLP

(57) ABSTRACT

A magnetic embolization apparatus for embolizing an aneurysm of a blood vessel includes a catheter with a distal portion, and a permanent magnet and an electromagnet carried by the distal portion to internally induce a magnetic field in the aneurysm to control a magnetic field controllable embolic to embolize the aneurysm. A related method of embolizing an aneurysm of a blood vessel includes delivering a magnetic-field controllable embolic into an aneurysm, and simultaneously inducing a magnetic field in the aneurysm with a permanent magnet and an electromagnet to embolize the aneurysm.

18 Claims, 2 Drawing Sheets

PERMANENT MAGNETIC AND ELECTROMAGNETIC APPARATUS FOR EMBOLIZING AN ANEURYSM WITH MAGNETICALLY CONTROLLABLE EMBOLIC AND METHOD

FIELD OF THE INVENTION

The invention relates, in general, to an apparatus and method for forming an occlusion in a mammalian body, and, in particular, to an apparatus and method for embolizing an aneurysm with a magnetically controllable substance.

BACKGROUND

Like all parts of the body, the brain is composed of living cells that require a blood supply to provide oxygen and nutrients. A hemorrhage in a blood vessel in the brain or in the space closely surrounding the brain is a common cause of strokes. Hemorrhage refers to bleeding into the brain, usually because of a problem with a blood vessel. The problem is often an aneurysm.

An aneurysm is an abnormal bulging outward of blood vessel wall. The wall may smoothly bulge outward in all directions (a fusiform aneurysm) or it may form a sack arising from one wall (a saccular aneurysm). If the aneurysm ruptures, a hemorrhage occurs. This can compress and irritate the surrounding blood vessels, resulting in a reduced supply of oxygen and nutrients to the cells, possibly causing a stroke.

Aneurysms can be treated from outside the blood vessel using surgical techniques or from inside the blood vessel using endovascular techniques. Endovascular treatment of an aneurysm is performed using a catheter. X-ray, magnetic resonance imaging (MRI) equipment, or other visualization equipment may be used to view the progress during the procedure.

A magnetically directable embolic such as an acrylic, iron-containing glue has been proposed to fill or obliterate aneurysms. The embolic is delivered by means of a catheter and is directed into an aneurysm with an external magnetic field generated by a permanent magnet or electrogmanetic device used for Stereotaxis prcedures such as a prototype device made by Stereotaxis Inc. of St. Louis, Mo. An example of such a device is shown and described in U.S. Pat. No. 6,014,580 to Blume, et al. Problems with this approach include that the Stereotaxis machine is cumbersome and expensive and, in some cases, the external magnetic field produced by the Stereotaxis machine is not strong enough to control delivery of the iron-containing, magnetically-directable glue into the aneurysm.

SUMMARY OF THE INVENTION

An aspect of the present invention involves a magnetic embolization apparatus for embolizing an aneurysm of a blood vessel. The magnetic embolization apparatus includes a catheter with a distal portion, and a permanent magnet and an electromagnet carried by the distal portion to internally induce a magnetic field in the aneurysm to control a magnetic field controllable embolic to embolize the aneurysm.

Implementations of the aspect of the invention described immediately above may include one or more of the following. The electromagnet is adapted to induce a magnetic field in a first direction to strengthen a magnetic field induced by the permanent magnet to embolize the aneurysm and in a second direction to counteract the magnetic field induced by the permanent magnet to assist in withdrawing the catheter from the aneurysm without removing any embolic. The distal portion includes a sealed tip to prevent a magnetic field controllable embolic from being drawn into the catheter. The permanent magnet is located circumferentially outside or inside the electromagnet. The catheter includes a wall with the permanent magnet and electromagnet located therein. A guide wire is slidably disposed in the catheter and carries the permanent magnet. The catheter includes a lumen that carries the permanent magnet.

Another aspect of the invention involves a method of embolizing an aneurysm of a blood vessel. The method includes delivering a magnetic-field controllable embolic into an aneurysm, and simultaneously inducing a magnetic field in the aneurysm with a permanent magnet and an electromagnet to embolize the aneurysm.

Implementations of the aspect of the invention described immediately above may include one or more of the following. A catheter includes a distal portion with the permanent magnet and the electromagnet located therein, and the step of simultaneously inducing a magnetic field in the aneurysm includes simultaneously inducing a magnetic field in the aneurysm with the permanent magnet and the electromagnet of the catheter to induce the magnetic filed in the aneurysm. The method further includes the steps of using the electromagnet to induce a magnetic field in a first direction to strengthen a magnetic field induced by the permanent magnet to embolize the aneurysm and in a second direction to counteract the magnetic field induced by the permanent magnet to assist in withdrawing the catheter from the aneurysm without removing any embolic. A guide wire is slidably disposed in the catheter and carries the permanent magnet, and the method further includes the step of introducing the permanent magnet into the aneurysm with the guide wire. The step of delivering a magnetic-field controllable embolic into the aneurysm is done with a second, separate microcatheter.

Other features and advantages of the invention will be evident from reading the following detailed description, which is intended to illustrate, but not limit, the invention.

BRIEF DESCRIPTION OF THE DRAWINGS

The drawings illustrate the design and utility of preferred embodiments of the present invention, in which similar elements are referred to by common reference numerals.

DETAILED DESCRIPTION OF THE PREFERRED EMBODIMENTS

Figure 1:
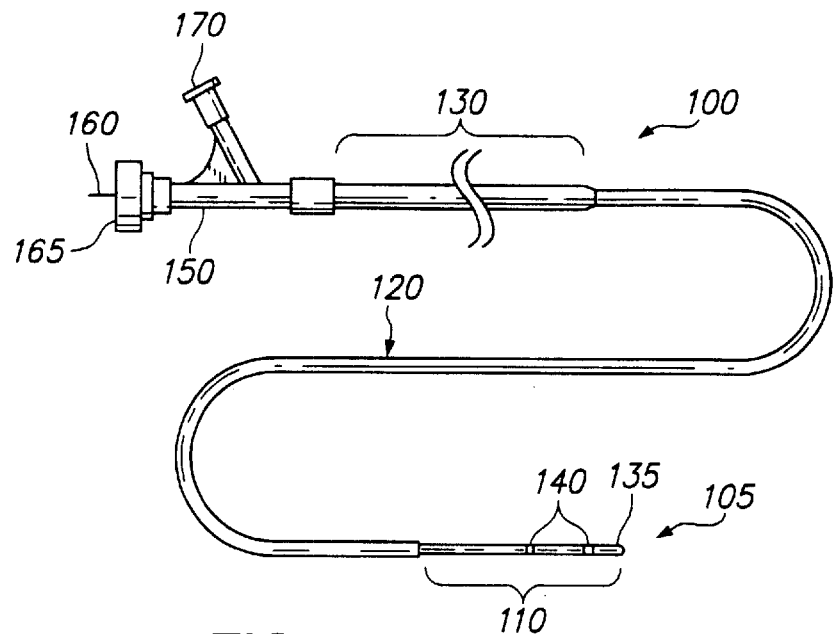
FIG. 1 is a side-elevational view of an embodiment of a catheter that may be used with the magnetic embolization apparatus.

With reference to FIG. 1, an exemplary multi-section catheter 100 that may be used to deliver a magnetic embolization apparatus 105, which is constructed in accordance with an embodiment of the invention, at a targeted aneurysm 107 (FIG. 2) will now be described. The magnetic embolization apparatus 105 induces a magnetic field in the aneurysm 107 to draw and retain a magnetically controllable embolic in the aneurysm 107. Although the invention will be described in terms of aneurysm treatment, it may also be adaptable for endovascular occlusion in arteries, veins, vascular malformations, and arteriovenous fistulas. The invention may also be used for forming an occlusion in other areas of a mammalian body.

The catheter 100 includes a distal section 110, an intermediate section 120, and a proximal section 130. The sections decrease in flexibility from the proximal section 130 to the distal section 110.

The distal section or portion 110 is very flexible and soft to allow deep penetration into the extraordinary convolutions of the neurological vasculature without trauma. The magnetic embolization apparatus 105 is located in the distal section 110 of the catheter 100 at a distal end 135. The distal section 110 may include one or more radio-opaque bands or markers 140 to allow viewing of the position of the distal section under fluoroscopy.

A luer assembly 150 at the proximal section 130 of the catheter 100 may accomodate a pusher, core, or guide wire 160. The wire 160 may be made of any well-known guide wire material in the art such as stainless steel. The luer assembly 150 may also include a fluid port 165 for connecting a fluid supply for introducing and/or removing a magnetically controllable embolic and a power port 170 for connecting the catheter 100 to a power supply. The magnetically controllable embolic may be delivered to the aneurysm site with a second, separate microcatheter (not shown). The catheter 100 may also include any well-known steering assembly in the art for delivering the magnetic embolization apparatus 105 to the targeted aneurysm 107.

Figure 2:
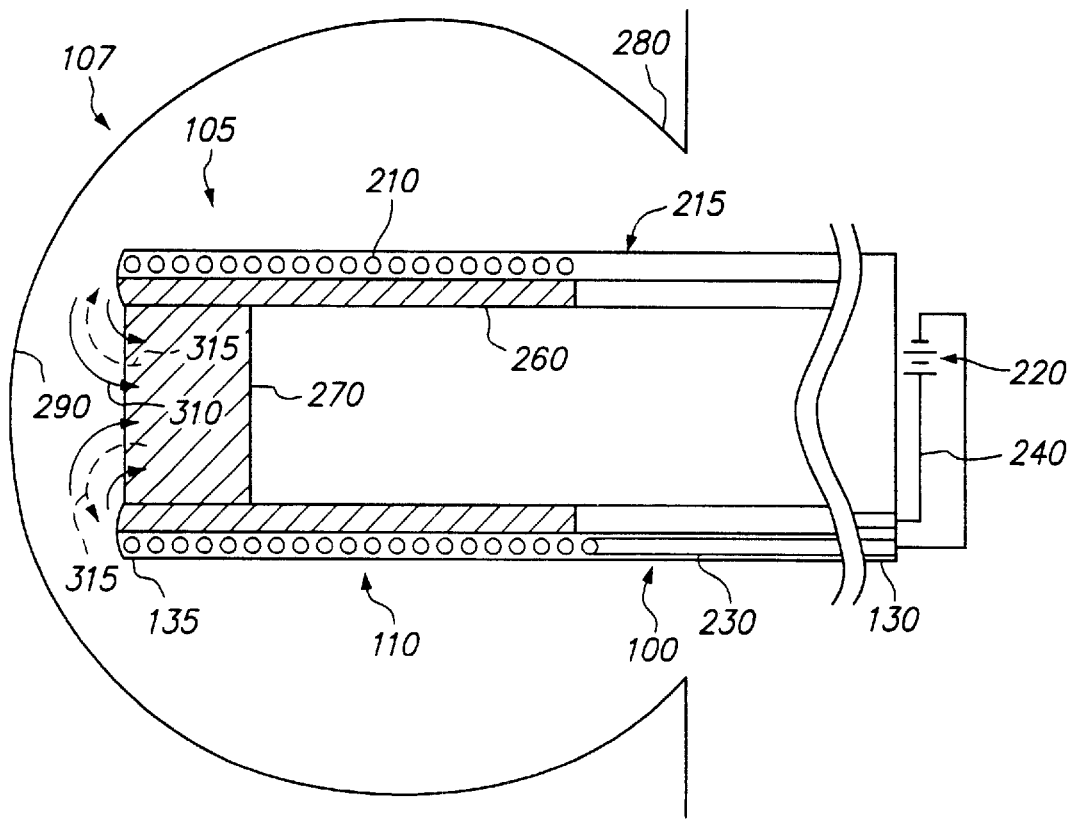
FIG. 2 is a cross-sectional view of a distal portion of the catheter illustrated in FIG. 1 in a blood vessel with an embodiment of the magnetic embolization apparatus shown disposed in an aneurysm.

With reference to FIG. 2, an embodiment of the magnetic embolization apparatus 105 will now be described. The apparatus 105 includes a coiled solenoid or induction electromagnet 210 located in a wall 215 of the catheter body, in the distal portion 110 of the catheter 100. Electrical current may be supplied to the electromagnet 210 by a power source 220 via a lead wire 230 and returned by a return wire 240 to induce a first magnetic field. Polarity through the electromagnet 210 may be reversed to induce a second magnetic field in an opposite direction from the first magnetic field. A ferrous filling layer or permanent magnet layer 260 may be located in the catheter wall 215, in the distal portion 110 of the catheter 100. The layer 260 may be used to help generate a stronger magnetic field at the end of the catheter 100 and/or help reverse the magnetic field to remove the catheter 100 at the end of the procedure. A sealed tip or plug 270 may be located at the distal end 135 of the catheter 110 to prevent the ferrous polymer from entering the catheter 110. The plug 270 is preferably made of a non-ferrous material. In an alternative embodiment, the plug 270 may be made of a ferrous material.

The magnetic embolization apparatus 105 will now be described in use. The catheter 100 is introduced into the vasculature of a patient via a cannula or introducer sheath and snaked through the vasculature of the patient to the targeted aneurysm 107 by any well-known method in the art. X-ray, fluoroscopy or other well-known visualization techniques may be used to assist the physician in directing the catheter 100 to the targeted aneurysm 107. The distal end 135 of the catheter 100 may be positioned at the aneurysm site adjacent a neck 280 of the aneurysm 107, at the neck 280 of the aneurysm 107, or within the aneurysm 107. Preferably, the distal end 135 of the catheter 100 is positioned into the aneurysm 107, near a dome 290 of the aneurysm 107.

Next, a magnetically controllable embolic such as a ferrous polymer (e.g., acrylic, iron-containing glue) that hardens over time is delivered to the aneurysm 107 via a separate, second microcatheter (not shown). In an alternative embodiment, the embolic may have a different composition.

The electromagnet 210 and ferrous filling/permanent magnet layer 260 are used to generate magnetic field lines 3 10 at the distal portion 110 of the catheter 100 for drawing and retaining the magnetically controllable embolic in the aneurysm 107 for embolization. The electromagnet 210 is actuated by supplying current by the power source 220 through the lead wire 230 to the electromagnet 210. The ferrous filling layer or permanent magnet layer 260 may help in inducing the magnetic field lines 310 for drawing and retaining the ferrous polymer in the aneurysm 107. The combined magnetic fields induced by the electromagnet 210 and the permanent magnet 260 provide sufficient attractive force for drawing and maintaining the magnetically controllable embolic in the aneurysm 107 for embolization purposes. The strength of the magnetic field 310 induced by the electromagnet 210 may be controlled by varying the power supplied to the electromagnet 210.

If the layer 260 is a ferrous filling layer, magnetic field 310 may be terminated after the embolic has hardened or polymerized a sufficient amount, and the catheter 100 may be withdrawn from the aneurysm site. If the layer 260 is a permanent magnet layer, the polarity of the electromagnet 210 may be reversed, causing opposite magnetic field lines 315 to counteract or cancel out the magnetic field 310 induced by the permanent magnetic layer 260 so that the catheter 100 can be withdrawn from the aneurysm site without removing any of the embolic from the anuerysm 107.

The electromagnet 210 may also be used to retrieve cured magnetically controllable embolic that may have escaped the aneurysm 107.

Figure 3:
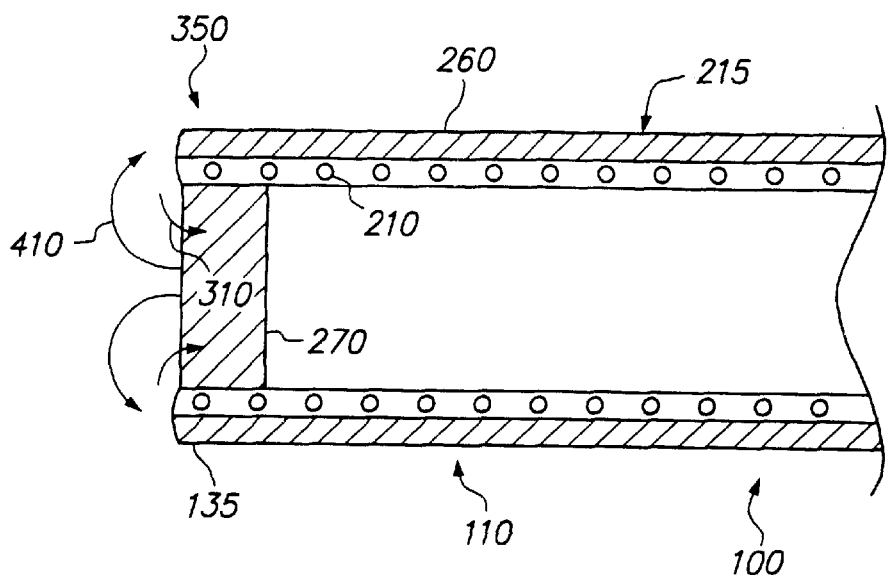
FIG. 3 is a cross-sectional view of a distal portion of a catheter with an additional embodiment of a magnetic embolization apparatus shown.

With reference to FIG. 3, a magnetic embolization apparatus 350 constructed in accordance with an additional embodiment of the invention and method of use is the same as that described above with respect to FIG. 2 for the magnetic embolization apparatus 105, except the electromagnet 210 is located circumferentially inside of the ferrous filling layer or permanent magnet layer 260 in the catheter wall 215. Locating the electromagnet 210 circumferentially inside of the ferrous filling layer or permanent magnet layer 260 helps to enable a stronger magnetic field in the aneurysm 107 for drawing and holding the embolic in the aneurysm 107 during embolization or for cancelling out a possible magnetic field 310 generated by a permanent magnet layer 260 for removing the catheter 100 without removing any of the embolic from the anuerysm 107.

Figure 4:
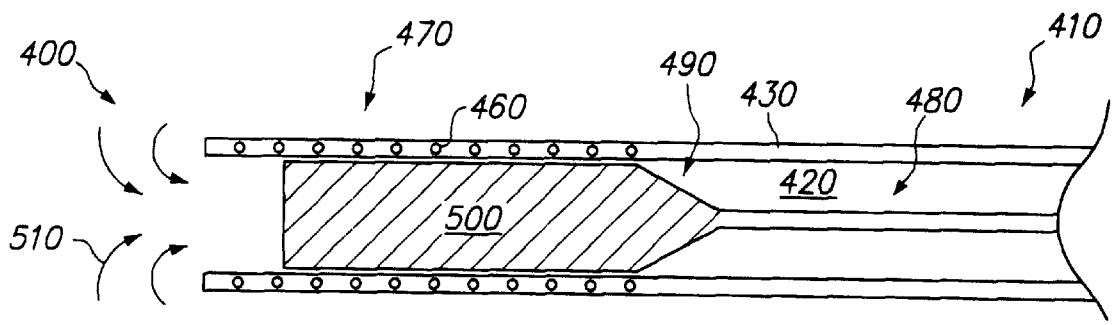
FIG. 4 is a cross-sectional view of a distal portion of a catheter including a further embodiment of a magnetic embolization apparatus shown.

With reference to FIG. 4, a magnetic embolization apparatus 400 constructed in accordance with another embodiment of the invention will now be described. The apparatus 400 is part of a catheter 410 having a lumen 420 defined by a lumen wall 430. The apparatus 400 includes a coiled solenoid or induction electromagnet 460 located in the lumen wall 430, in a distal portion 470 of the catheter 410. A guide wire 480, which may be the same as the guide wire 160 described above, may be slidably disposed within the lumen 420. At least a distal portion 490 of the guide wire 480 includes a ferrous portion or permanent magnet 500.

In use, the magnetic embolization apparatus 400 is snaked through the patient's vasculature to the targeted aneurysm site. The ferrous polymer is delivered to the aneurysm 107 through a separate, second microcatheter. Magnetic field lines 510 induced from the ferrous portion or permanent magnet 500 cause the ferrous polymer to be drawn into and retained within the aneurysm 107. The ferrous portion or permanent magnet 500 may be maintained within the distal portion 470 of the catheter 410 or may be deployed from the catheter 410, into the aneurysm 107 for embolization purposes. To remove the catheter 410 from the aneurysm 107, the solenoid 460 may be actuated to induce a magnetic field that overcomes, counteracts, or cancels out the magnetic field 510 of the ferrous portion or permanent magnet 500.

In an alternative embodiment, the solenoid 460 may be actuated to create, in conjunction with the magnetic field 510 induced from the ferrous portion or permanent magnet 500, a stronger magnetic field for drawing and retaining the ferrous polymer in the aneurysm 107. To remove the catheter 410 from the aneurysm 107, the polarity through the solenoid 460 may be reversed to overcome, counteract, or cancel out the magnetic field of the ferrous portion or permanent magnet 500.

Figure 5:
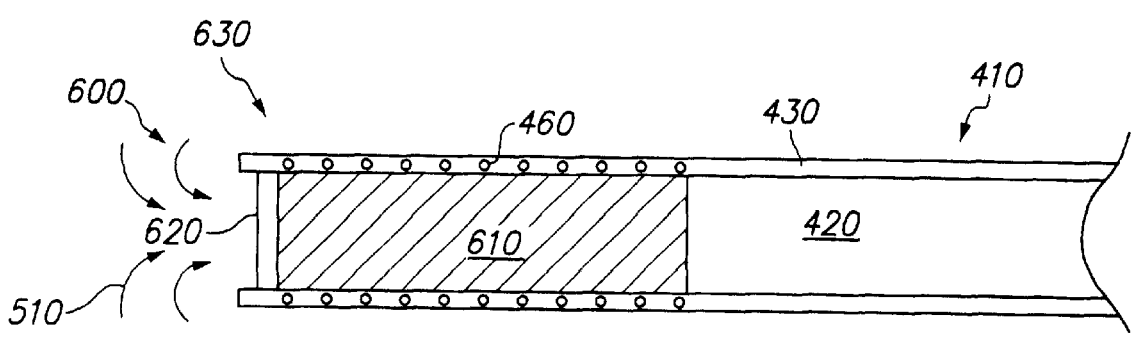
FIG. 5 is a cross-sectional view of a distal portion of a catheter including a still further embodiment of a magnetic embolization apparatus shown.

With reference to FIG. 5, a magnetic embolization apparatus 600 constructed in accordance with a further embodiment of the invention will now be described. The magnetic embolization apparatus 600 is similar to the magnetic embolization apparatus 400 described above, except the guide wire 480 is replaced with a ferrous portion or permanent magnet 610. A plug 620 may be located at a distal end 630 of the lumen 420 to prevent the ferrous polymer from entering the lumen 420.

The method of use for the magnetic embolization apparatus 600 is the same as that described above with respect to the magnetic embolization apparatus 400, except the ferrous portion or permanent magnet 610 of the apparatus 600 can not be deployed into the aneurysm 107 apart from the catheter 410.

Thus, the magnetic embolization apparatus embodiments described above include a permanent magnet combined with an electromagnet to induce a strong enough magnetic field to draw and maintain the magnetically controllable embolic in the aneurysm 107 for embolization purposes. The polarity of the electromagnet may be reversed to create a magnetic field that counteracts the magnetic field of the permanent magnet to facilitate withdrawal of the catheter from the aneurysm site without removing any of the embolic.

While embodiments and applications of this invention have been shown and described, it would be apparent to those in the field that many more modifications are possible without departing from the inventive concepts herein. The invention, therefore, is not to be restricted except in the spirit of the appended claims.

What is claimed is:

1. A magnetic embolization apparatus for embolizing an aneurysm of a blood vessel, comprising:
    a catheter including a distal portion;
    a permanent magnet and an electromagnet carried by the distal portion of the catheter to internally induce a magnetic field in the aneurysm to control a magnetic field controllable embolic to embolize the aneurysm.

2. The apparatus of claim 1, wherein the electromagnet is adapted to induce a magnetic field in a first direction to strengthen a magnetic field induced by the permanent magnet to embolize the aneurysm and in a second direction to counteract the magnetic field induced by the permanent magnet to assist in withdrawing the catheter from the aneurysm without removing any embolic.

3. The apparatus of claim 1, wherein the distal portion includes a sealed tip to prevent a magnetic field controllable embolic from being drawn into the catheter.

4. The apparatus of claim 1, wherein the permanent magnet is located circumferentially outside the electromagnet.

5. The apparatus of claim 1, wherein the permanent magnet is located circumferentially inside the electromagnet.

6. The apparatus of claim 1, wherein the catheter includes a wall with the permanent magnet and electromagnet.

7. The apparatus of claim 1, further including a guide wire slidably disposed in the catheter and carrying the permanent magnet.

8. The apparatus of claim 1, wherein the catheter includes a lumen that carries the permanent magnet.

9. A method of embolizing an aneurysm of a blood vessel, comprising:
    delivering a magnetic-field controllable embolic into an aneurysm within a body;
    placing a permanent magnet and an electromagnet within the body; and
    simultaneously inducing a magnetic field in the aneurysm with the permanent magnet and the electromagnet to embolize the aneurysm.

10. The method of claim 9, wherein a catheter includes a distal portion with the permanent magnet and the electromagnet located therein, and the step of simultaneously inducing a magnetic field in the aneurysm includes simultaneously inducing a magnetic field in the aneurysm with the permanent magnet and the electromagnet of the catheter to induce the magnetic field in the aneurysm.

11. The method of claim 10, further including the steps of using said electromagnet to induce a magnetic field in a first direction to strengthen a magnetic field induced by the permanent magnet to embolize the aneurysm and in a second direction to counteract the magnetic field induced by the permanent magnet to assist in withdrawing the catheter from the aneurysm without removing any embolic.

12. The method of claim 10, wherein the distal portion includes a sealed tip to prevent a magnetic field controllable embolic from being drawn into the catheter.

13. The method of claim 10, wherein the permanent magnet is located circumferentially outside the electromagnet.

14. The method of claim 10, wherein the permanent magnet is located circumferentially inside the electromagnet.

15. The method of claim 10, wherein the catheter includes a wall with the permanent magnet and electromagnet.

16. The method of claim 10, further including a guide wire slidably disposed in the catheter and carrying the permanent magnet, the method further including the step of introducing the permanent magnet into the aneurysm with the guide wire.

17. The method of claim 10, wherein the catheter includes a lumen that carries the permanent magnet.

18. The method of claim 10, wherein the step of delivering a magnetic-field controllable embolic into the aneurysm is done with a second, separate microcatheter.

* * * * *